(12) United States Patent
Farman et al.

(10) Patent No.: US 10,159,684 B2
(45) Date of Patent: Dec. 25, 2018

(54) PHARMACEUTICAL COMPOSITIONS FOR PREVENTING GLUCOCORTICOID-INDUCED CORNEAL THINNING

(71) Applicants: INSERM (INSTITUT NATIONAL DE LA SANTE ET DE LA RECHERCHE MEDICALE), Paris (FR); UNIVERSITE PARIS DESCARTES, Paris (FR); UNIVERSITE PIERRE ET MARIE CURIE (PARIS 6), Paris (FR); ASSISTANCE PUBLIQUE—HOPITAUX DE PARIS (APHP), Paris (FR)

(72) Inventors: Nicolette Farman, Paris (FR); Frederic Jaisser, Paris (FR); Francine Behar-Cohen, Paris (FR); Selin Aractingi, Paris (FR); Van Tuan Nguyen, Paris (FR)

(73) Assignees: INSTITUT NATIONAL DE LA SANTE ET DE LA RECHERCHE MEDICALE (INSERM), Paris (FR); UNIVERSITE PARIS DESCARTES, Paris (FR); UNIVERSITE PIERRE ET MARIE CURIE (PARIS 6), Paris (FR); ASSISTANCE PUBLIQUE—HOPITAUX DE PARIS (APHP), Paris (FR)

( * ) Notice: Subject to any disclaimer, the term of this patent is extended or adjusted under 35 U.S.C. 154(b) by 0 days.

(21) Appl. No.: 15/616,971

(22) Filed: Jun. 8, 2017

(65) Prior Publication Data
US 2017/0273992 A1   Sep. 28, 2017

Related U.S. Application Data

(62) Division of application No. 14/899,162, filed as application No. PCT/EP2014/062995 on Jun. 20, 2014, now Pat. No. 9,730,948.

(30) Foreign Application Priority Data
Jun. 21, 2013  (EP) .................................... 13305851

(51) Int. Cl.
A61K 31/585   (2006.01)
A61K 31/573   (2006.01)
A61K 9/00     (2006.01)
A61K 45/06    (2006.01)

(52) U.S. Cl.
CPC .......... *A61K 31/585* (2013.01); *A61K 9/0048* (2013.01); *A61K 31/573* (2013.01); *A61K 45/06* (2013.01); *A61K 9/0014* (2013.01)

(58) Field of Classification Search
CPC ............................ A61K 31/585; A61K 31/573
USPC .................................................. 514/175, 179
See application file for complete search history.

(56) References Cited

PUBLICATIONS

Bousquet et al., "The Aldosterone-Minerlocorticoid Receptor Pathway Exerts Anti-Inflammatory Effects in Endotoxin-Induced Uveitis", Plos One, vol. 7, No. 11, p. e49036 (Year: 2011).*

* cited by examiner

*Primary Examiner* — Kevin E Weddington
(74) *Attorney, Agent, or Firm* — W & C IP

(57) ABSTRACT

The present invention relates to method and pharmaceutical compositions for preventing glucocorticoid-induced corneal or skin thinning. In particular, the present invention relates to a mineralocorticoid receptor antagonist for topical use in a method for preventing or reducing glucocorticoid-induced corneal or skin thinning in a subject in need thereof. The invention also relates to a topical pharmaceutical composition comprising an amount of at least one glucocorticoid and an amount of at least one mineralocorticoid receptor antagonist or inhibitor of MR expression for use in a method for treating an inflammatory skin disease or an inflammatory disease of the cornea or of the anterior segment of the eye in a subject in need thereof.

6 Claims, 2 Drawing Sheets

PHARMACEUTICAL COMPOSITIONS FOR PREVENTING GLUCOCORTICOID-INDUCED CORNEAL THINNING

CROSS-REFERENCE TO RELATED APPLICATIONS

This application is a divisional application of U.S. Ser. No. 14/899,162 filed Dec. 17, 2015, now U.S. Pat. No. 9,730,948, which itself was a Rule 371 national stage filing from PCT/EP2014/062995 filed Jun. 20, 2014 that claimed priority to European Application 13305851.1 filed Jun. 21, 2013.

FIELD OF THE INVENTION

The present invention relates to method and pharmaceutical compositions for preventing glucocorticoid-induced corneal or skin thinning.

BACKGROUND OF THE INVENTION

Glucocorticoids are highly effective for the topical treatment of inflammatory skin diseases and are a widely used class of anti-inflammatory drugs. Their long-term use, however, is accompanied by severe and partially irreversible adverse effects with skin thinning being the most prominent. General ski thinning consists of a reduction in epidermal and dermal thickness, regression of the sebaceous glands, subcutaneous fat loss, and muscle-layer atrophy. These changes are typically observed following 2 to 3 weeks of moderate-to high-potency topical glucocorticoid use. A single application of a very potent topical glucocorticoid can cause an ultrasonographically detectable decrease in skin thickness that lasts up to 3 days. Even low-potency topical glucocorticoids can cause slight skin thinning that often reverses upon discontinuation of the drugs. The cutaneous effects of glucocorticoid treatment are due to suppression of the proliferation and the extracellular matrix (ECM) protein synthesis of kerationcytes and fibroblast. The intercellular lipid layers are also reduced by glucocorticoids caused by the decreased synthesis of epidermal lipids, like ceramides, cholesterol and fatty acids. Thereby the stratum corneum gets thinner, followed by an increased transepidermal water loss. The skin loses its barrier function, its tensile strength and elasticity caused by the water loss and the degraded extracellular matrix. There is therefore a long felt medical need to alleviate these severe and unpleasant properties of glucocorticoids during treatment of inflammatory skin diseases. Glucocorticoid administration on the eye may also result in alterations of the epithelial surface (similar to keratinocytes) and conjunctiva, leading to keratitis.

SUMMARY OF THE INVENTION

The present invention relates to method and pharmaceutical compositions for preventing glucocorticoid-induced corneal or skin thinning.

DETAILED DESCRIPTION OF THE INVENTION

The inventors show that that excess mineralocorticoid receptor (MR) in keratinocytes leads to reduced epidermal thickness that is aggravated at birth in mice with MR overexpression in keratinocytes. Moreover the inventors show that topical administration of a glucocorticoid (i.e. clobetasol) in normal adult mice induces a drastic reduction of epidermal thickness reproducing the well-known glucocorticoid-induced skin thinning. They finally show that glucocorticoid-induced skin thinning may be reduced when the mice are treated with the glucocorticoid in combination with a mineralocorticoid receptor antagonist (i.e. spironolactone). The same effects were reproduced with human skin explants. Besides, the conical epithelium expresses the mineralocorticoid receptor (Sainte Marie et al, Am. J. Pathol 2007). Glucocorticoids administered in the eye also exerts negative effects at the eye surface, possibly leading to corneal and conjuctival alterations and erosion of the corneal epithelium and conjunctive. Local application of MR antagonists may also be beneficial to improve the reduced corneo-conjunctival epithelium thickness.

Accordingly an aspect of the present invention relates to a mineralocorticoid receptor antagonist for use in a method for preventing or reducing glucocorticoid-induced conical or skin thinning in a subject in need thereof.

In some embodiments, the subject suffers of an inflammatory skin disease for which topical administration of glucocortocoid is prescribed. Examples of skin diseases include but are not limited to eczema, psoriasis, allergic dermatitis, neurodermatitis, pruritis, exfoliative dermatitis, pemphigus and hypersensitivity reactions.

In some embodiments, the subject suffers of an inflammatory disease of the cornea or of the anterior segment of the eye for which topical administration of glucocorticoid is prescribed. Examples of ocular disease include but are not limited to uveitis, blepharitis, conjunctivitis, scleritis, and postoperative inflammation.

As used herein the term "glucocorticoid" has it general meaning in the art and refers to compounds that bind and activate the glucocorticoid receptor (GR). Glucocorticoid can also bind and activate mineralocorticoid receptor (MR). Example of glucocorticoids include but are not limited to 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, anecortave acetate and any of their derivatives.

As used herein, the term "mineralocorticoid receptor" or "MR" has its general meaning in the art and refers to the nuclear receptor subfamily 3, group C, member 2, (NR3C2) that is a receptor with high affinity for mineralocorticoids. The mineralocorticoid receptor is also called aldosterone receptor.

As used herein the term "MR antagonist" has its general meaning in the art. The MR antagonistic of a compound may be determined using various methods as described in J. Souque A, Wurtz J M, Moras D, Rafestin-Oblin M E. Mol Endocrinol. 2000 August; 14(8):1210-21; Fagart J, Seguin C, Pinon G M, Rafestin-Oblin M E. Mol Pharmacol. 2005 May; 67(5):1714-22 or Hellal-Levy C, Fagart J, Souque A, Wurtz J M, Moras D, Rafestin-Oblin M E. Mol Endocrinol. 2000 August; 14(8):1210-21. Typically, the transfection of the human mineralocorticoid receptor in COS cells together with a luciferase-expressing reporter gene allows to measure its transactivation activity in the presence of a candidate compound. In the context of the present invention, mineralocorticoid receptor antagonists are preferably selective for the mineralocorticoid receptor as compared with the related receptors such as androgen receptor, estrogen receptors, glucocorticoid receptor, progesterone receptor, thyroid hormone receptors, peroxisome proliferator-activated receptors, retinoic acid receptor, farnesoid x receptor, pregnane x receptor, liver X receptor, vitamin D receptor, retinoid x receptor and the constitutive androstane receptor. By "selective" it is meant that the affinity of the antagonist for the mineralocorticoid receptor is at least 10-fold, preferably 25-fold, more preferably 100-fold, still preferably 500-fold higher than the affinity for the related receptors. MR antagonists constitute a class o pharmacological compounds that are well known by the skilled artisan.

For example, the mineralocorticoid receptor antagonists according to the invention generally are spirolactone-type steroidal compounds. The term "spirolactone-type" is intended to characterize a structure comprising a lactone moiety attached to a steroid nucleus, typically at the steroid "D" ring, through a Spiro bond configuration. A subclass of spirolactone-type mineralocorticoid receptor antagonist compounds consists of epoxy-steroidal mineralocorticoid receptor antagonist compounds such as eplerenone. Another subclass of spirolactone-type antagonist compounds consists of non-epoxy-steroidal mineralocorticoid receptor antagonist compounds such as spironolactone.

The epoxy-steroidal mineralocorticoid receptor antagonist compounds used in the method of the present invention generally have a steroidal nucleus substituted with an epoxy-type moiety. The term "epoxy-type" moiety is intended to embrace any moiety characterized in having an oxygen atom as a bridge between two carbon atoms.

The term "steroidal," as used in the phrase "epoxy-steroidal," denotes a nucleus provided by a cyclopentenophenanthrene moiety, having the conventional "A", "B", "C", and "D" rings. The epoxy-type moiety may be attached to the cyclopentenophenanthrene nucleus at any attachable or substitutable positions, that is, fused to one of the rings of the steroidal nucleus or the moiety may be substituted on a ring member of the ring system. The phrase "epoxy-steroidal" is intended to embrace a steroidal nucleus having one or a plurality of epoxy-type moieties attached thereto.

Epoxy-steroidal mineralocorticoid receptor antagonists suitable for use in the present methods include a family of compounds having an epoxy moiety fused to the "C" ring of the steroidal nucleus. Examples include 20-spiroxane compounds characterized by the presence of a 9α, 11α-substituted epoxy moiety, such as:

Pregn-4-ene-7,21-dicarboxylic acid, 9,11-epoxy-17-hydroxy-3-oxo-,γ-lactone, methyl ester, (7α, 11α, 17β)

Pregn-4-ene-7,21-dicarboxylic acid, 9,11-epoxy-17-hydroxy-3-oxo-,dimethyl ester, (7α,11α,17β)

3' H-cyclopropa[6,7]pregna-4,6-diene-21-carboxylic acid,9,11-epoxy-6,7-dihydro-17-hydroxy-3-oxo-, γ-lactone, (6β, 7β,11α,17β)

Pregn-4-ene-7,21-dicarboxylic acid,9,11-epoxy-17-hydroxy-3-oxo-,7-(1-methylethyl) ester,monopotassium salt, (7α,11α,17β)

Pregn-4-ene-7,21-dicarboxylic acid,9,11-epoxy-17-hydroxy-3-oxo-,7-methylethyl) ester,monopotassium salt, (7α,11α,17β)

3' H-cyclopropa[6,7]pregna-1,4,6-triene-21-carboxylic acid,9,11-epoxy-6,7-dihydro-17-hydroxy-3-oxo-, γ-lactone(6β,7β,11α)

3' H-cyclopropa[6,7]pregna-4,6-diene-21-carboxylic acid, 9,11-epoxy-6,7-dihydro-17-hydroxy-3-oxo-, methyl ester, (6β,7β,11α,17β)

3' H-cyclopropa[6,7]pregna-4,6-diene-21-carboxylic acid, 9,11-epoxy-6,7-dihydro-17-hydroxy-3-oxo-, monopotassium salt, (6β,7β,11α,17β)

3' H-cyclopropa[6,7]pregna-1,4,6-triene-21-carboxylic acid, 9,11-epoxy-6,7-dihydro-17-hydroxy-3-oxo-, γ-lactone(6β,7β,11α,17β)

Pregn-4-ene-7,21-dicarboxylic acid,9,11-epoxy-17-hydroxy-3-oxo-,γ-lactone, ethyl ester, (7α,11α,17β)

Pregn-4-ene-7,21-dicarboxylic acid,9,11-epoxy-17-hydroxy-3-oxo-,γ-lactone, 1-methylethyl ester (7α,11α, 17β)

A particular benefit of using epoxy-steroidal mineralocorticoid receptor antagonists, as exemplified by eplerenone, is the high selectivity of this group of mineralocorticoid receptor antagonists for the mineralocorticoid receptor. The superior selectivity of eplerenone results in a reduction in side effects that can be caused by mineralocorticoid receptor antagonists that exhibit non-selective binding to related receptors, such as androgen or progesterone receptors.

These epoxy steroids may be prepared by procedures described in Grob et al., U.S. Pat. No. 4,559,332. Additional processes for the preparation of 9, 11-epoxy steroidal compounds and their salts are disclosed in Ng et al., WO97/21720 and Ng et al., WO98/25948.

Of particular interest is the compound eplerenone ((Pregn-4-ene-7,21-dicarboxylic acid, 9,11-epoxy-17-hydroxy-3-oxo-,γ-lactone, methyl ester, (7α,11α,17β)) (CAS No. 107724-20-9), also known as epoxymexrenone. Eplerenone is a mineralocorticoid receptor antagonist and has a higher selectivity for mineralocorticoid receptors than does, for example, spironolactone. Selection of eplerenone as the mineralocorticoid receptor antagonist in the present method would be beneficial to reduce certain side-effects such as gynecomastia that occur with use of mineralocorticoid receptor antagonists having less specificity.

Non-epoxy-steroidal mineralocorticoid receptor antagonists suitable for use in the present methods include a family of spirolactone-type compounds defined by Formula I:

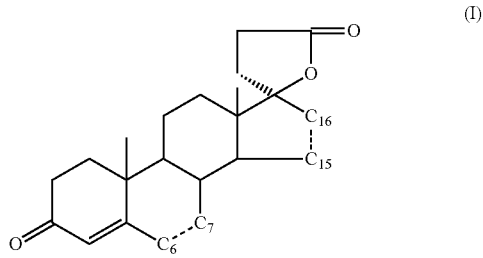

(I)

Wherein:

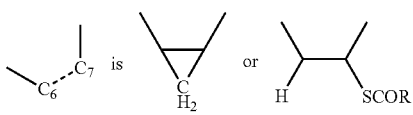

R is lower alkyl of up to 5 carbon atoms, and

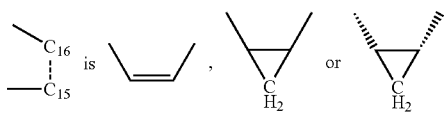

Lower alkyl residues include branched and unbranched groups, for example, methyl, ethyl and n-propyl.

Specific compounds of interest within Formula I are the following:

7α-acetylthio-3-oxo-4,15-androstadiene-[17(β-1')-spiro-5']perhydrofuran-2'-one;

3-oxo-7α-propionylthio-4,15-androstadiene-[17((β-1')-spiro-5']perhydrofuran-2'-one;

6β,7β-methylene-3-oxo-4,15-androstadiene-[17((β-1')-spiro-5']perhydrofuran-2'-one;

15α,16α-methylene-3-oxo-4,7α-propionylthio-4-androstene[17(β-1')-spiro-5']perhydrofuran-2'-one;

6β,7β,15α,16α-dimethylene-3-oxo-4-androstene[17(β-1')-spiro-5']-perhydrofuran-2'-one;

7α-acetylthio-15β,16β-Methylene-3-oxo-4-androstene-[17(β-1')-spiro-5']perhydrofuran-2'-one;

15β,16β-methylene-3-oxo-7β-propionylthio-4-androstene-[17(β-1')-spiro-5']perhydrofuran-2'-one; and 6β,7β,15β,16β-dimethylene-3-oxo-4-androstene-[17(β-1')-spiro-5']perhydrofuran-2'-one.

Methods to make compounds of Formula I are described in U.S. Pat. No. 4,129,564 to Wiechart et al. issued on 12 Dec. 1978.

Another family of non-epoxy-steroidal compounds of interest is defined by Formula II:

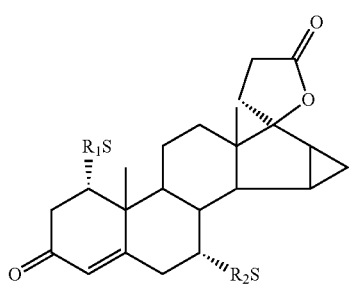

wherein R1 is C1-3-alkyl or C1-3 acyl and R2 is H or C1-3-alkyl.

Specific compounds of interest within Formula II are the following:

1α-acetylthio-15β,16β-methylene-7α-methylthio-3-oxo-17α-pregn-4-ene-21,17-carbolactone; and 15β,16β-methylene-1α,7α-dimethylthio-3-oxo-17α-pregn-4-ene-21,17-carbolactone.

Methods to make the compounds of Formula II are described in U.S. Pat. No. 4,789,668 to Nickisch et al. which issued 6 Dec. 1988.

Yet another family of non-epoxy-steroidal compounds of interest is defined by a structure of Formula III:

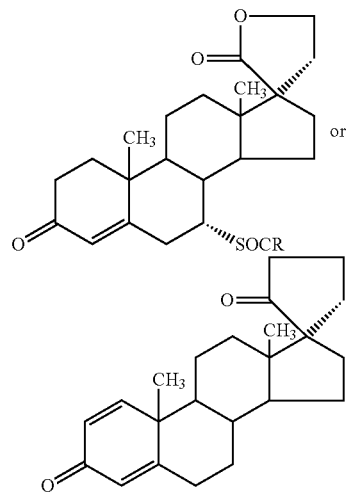

wherein R is lower alkyl, examples of which include lower alkyl groups of methyl, ethyl, propyl and butyl. Specific compounds of interest include:

3β,21-dihydroxy-17α-pregna-5,15-diene-17-carboxylic acid γ-lactone;

3β,21-dihydroxy-17α-pregna-5,15-diene-17-carboxylic acid γ-lactone 3-acetate;

3β,21-dihydroxy-17α-pregn-5-ene-17-carboxylic acid γ-lactone;

3β,21-dihydroxy-17α-pregn-5-ene-17-carboxylic acid γ-lactone 3-acetate;

21-hydroxy-3-oxo-17α-pregn-4-ene-17-carboxylic acid γ-lactone;

21-hydroxy-3-oxo-17α-pregna-4,6-diene-17-carboxylic acid γ-lactone;

21-hydroxy-3-oxo-17α-pregna-1,4-diene-17-carboxylic acid γ-lactone;

7α-acylthio-21-hydroxy-3-oxo-17α-pregn-4-ene-17-carboxylic acid γ-lactone; and

7α-acetylthio-21-hydroxy-3-oxo-17α-pregn-4-ene-17-carboxylic acid γ-lactone.

Methods to make the compounds of Formula III are described in U.S. Pat. No. 3,257,390 to Patchett which issued 21 Jun. 1966.

Still another family of non-epoxy-steroidal compounds of interest is represented by Formula IV:

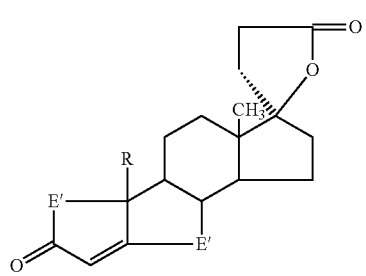

wherein E' is selected from the group consisting of ethylene, vinylene and (lower alkanoyl)thioethylene radicals, E" is selected from the group consisting of ethylene, vinylene, (lower alkanoyl)thioethylene and (lower alkanoyl) thiopropylene radicals; R is a methyl radical except when E' and E" are ethylene and (lower alkanoyl) thioethylene radicals, respectively, in which case R is selected from the group consisting of hydrogen and methyl radicals; and the selection of E' and E" is such that at least one (lower alkanoyl)thio radical is present.

One family of non-epoxy-steroidal compounds within Formula IV is represented by Formula V:

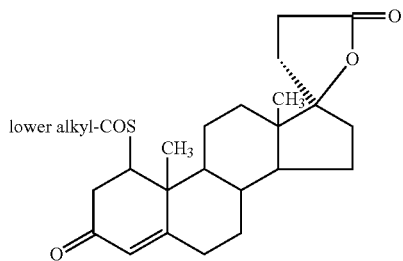

Another compound of Formula V is 1-acetylthio-17α-(2-carboxyethyl)-17β-hydroxy-androst-4-en-3-one lactone.

Another family of non-epoxy-steroidal compounds within Formula IV is represented by Formula VI:

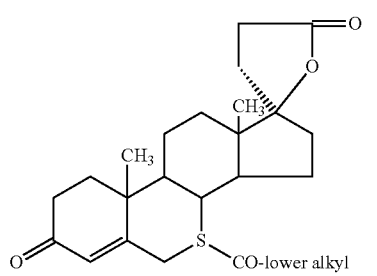

Exemplary compounds within Formula VI include the following:

7α-acetylthio-17α-(2-carboxyethyl)-17β-hydroxy-androst-4-en-3-one lactone:

7β-acetylthio-17α-(2-carboxyethyl)-17β-hydroxy-androst-4-en-3-one lactone;

1α,7α-diacetylthio-17α-(2-carboxyethyl)-17β-hydroxy-androsta-4,6-dien-3-one lactone;

7α-acetylthio-17αe-(2-carboxyethyl)-17β-hydroxy-androsta-1,4-dien-3-one lactone;

7α-acetylthio-17α-(2-carboxyethyl)-17β-hydroxy-19-norandrost-4-en-3-one lactone; and 7α-acetylthio-17α-(2-carboxyethyl)-17β-hydroxy-6α-methylandrost-4-en-3-one lactone.

In Formulae IV-VI, the term "alkyl" is intended to embrace linear and branched alkyl radicals containing one to about eight carbons. The term "(lower alkanoyl)thio" embraces radicals of the formula lower alkyl

Of particular interest is the compound spironolactone (17-hydroxy-7α-mercapto-3-oxo-17α-pregn-4-ene-21-carboxylic acid γ-lactone acetate) having the following structure:

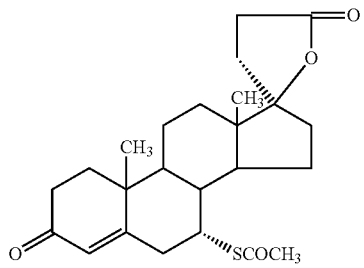

Methods to make compounds of Formulae IV-VI are described in U.S. Pat. No. 3,013,012 to Cella et al. which issued 12 Dec. 1961. Spironolactone is sold by G. D. Searle & Co. Skokie, Ill., under the trademark "ALDACTONE", in tablet dosage form at doses of 25 mg, 50 mg and 100 mg per tablet.

Another family of steroidal mineralocorticoid receptor antagonists is exemplified by drospirenone, (6R-(6α, 7α, 8β, 9α, 10β, 13β, 14α, 15α, 16α, 17β))-1,3', 4', 6, 7, 8, 9, 10, 11, 12, 13, 14, 15, 16, 20, 21-hexadecahydro-10, 13-dimethylspiro [17H-dicyclopropa(6,7:15,16)cyclopenta(a) phenanthrenc-17,2' (5' H)-furan)-3,5' (2H)-dione, CAS registration number 67392-87-4. Methods to make and use drospirenone are described in patent GB 1550568 1979, priority DE 2652761 1976.

Crystalline forms that are easily handled, reproducible in form, easily prepared, stable, and which are non-hygroscopic have been identified for the mineralocorticoid receptor antagonist eplerenone. These include Form H, Form L, various crystalline solvates and amorphous eplerenone. These forms, methods to make these forms, and use of these forms in preparing compositions and medicaments, are disclosed in Barton et al., WO 01/41535 and Barton et al., WO 01/42272 both incorporated herein in their entirety.

Mineralocorticoid receptor antagonists according to the invention may also be non-steroidal. For example, classes of non-steroidal MR antagonists have just begun to emerge over the past few years (Meyers, Marvin J1; Hu, Xiao Expert Opinion on Therapeutic Patents, Volume 17, Number 1, January 2007, pp. 17-23(7) and Piotrowski D W. Mineralocorticoid Receptor Antagonists for the Treatment of Hypertension and Diabetic Nephropathy J. Med. Chem. 2012, 55, 7957-7966). For instance, dihydropyrymidines have been shown to display MR antagonism (Activation of Mineralocorticoid Receptors by Exogenous Glucocorticoids and the Development of Cardiovascular Inflammatory Responses in Adrenalectomized Rats. Young M J, Morgan J, Brolin K, Fuller P J, Funder J W. Endocrinology. 2010 Apr. 21). Furthermore, Arhancet el al. disclose other class of non-steroidal M R antagonists (Arhancet G B, Woodard S S, Dietz J D, Garland D J, Wagner G M, Iyanar K, Collins J T, Blinn J R, Numann R E, Hu X, Huang H C. Stereochemical Requirements for the Mineralocorticoid Receptor Antagonist Activity of Dihydropyridines. J Med Chem. 2010 Apr. 21). Other exemplary non-steroidal mineralocorticoid receptor antagonists include but are not limited to those described in US 20090163472 WO2004052847, WO 2008053300 WO2008104306, WO2007025604, WO201264631, WO2008126831, WO2012008435, WO2010104721, WO200985584, WO200978934, WO2008118319, WO200917190, WO200789034, WO2012022121, WO2012022120, WO2011141848 and WO200777961 that are hereby incorporated by reference into the present disclosure.
In a particular embodiment the mineralocorticoid receptor antagonist is selected from the group consisting of:
BR-4628
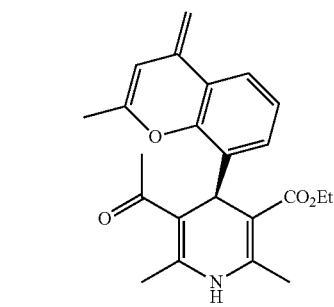
BAY 94-8862
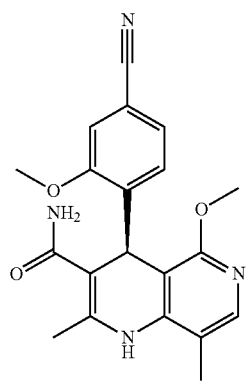
PF-3882845
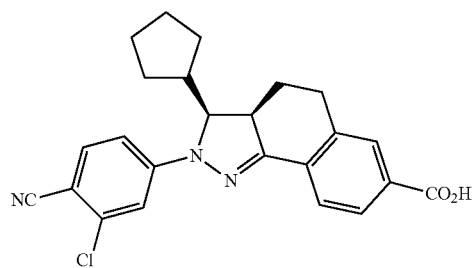
SM-368229
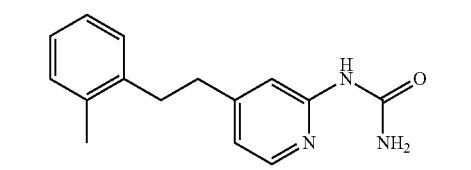
1
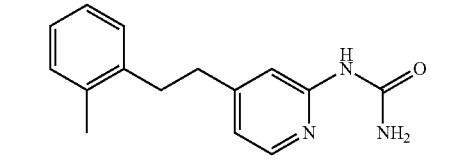
-continued
2
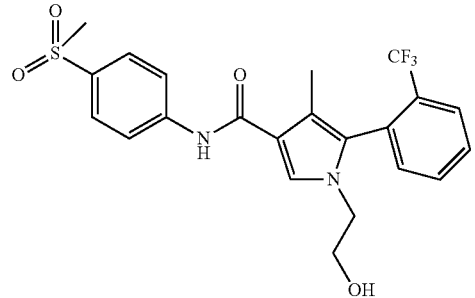
3
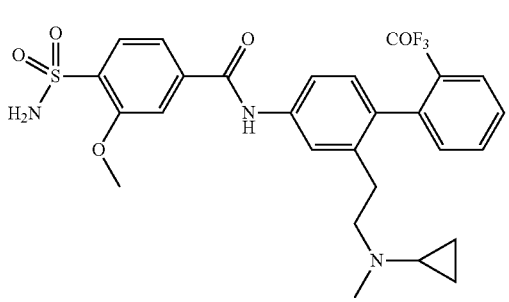
4
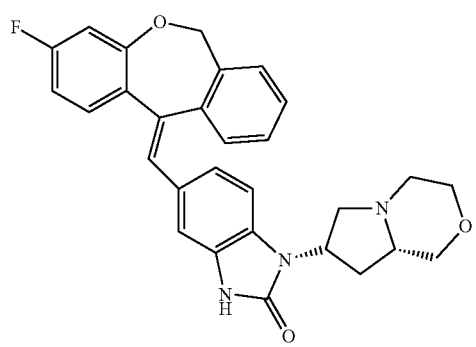
5
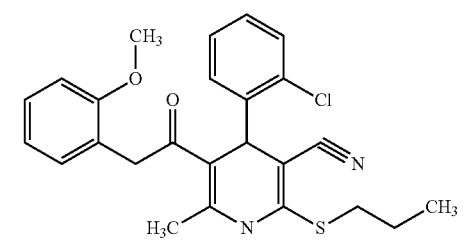
6
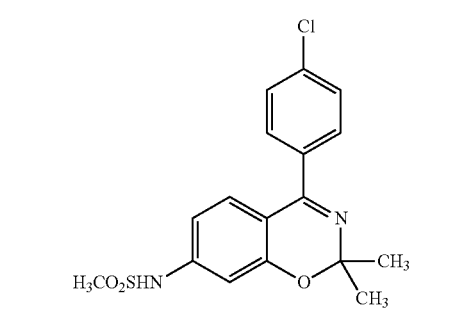

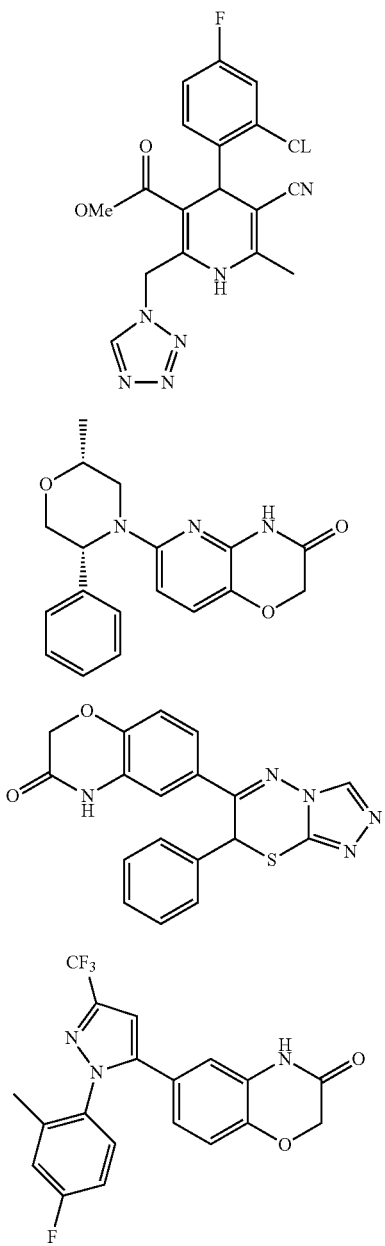

The present invention relates to an inhibitor of mineralocorticoid receptor gene expression for use in a method for preventing or reducing glucocorticoid-induced corneal or skin thinning in a subject in need thereof.

An "inhibitor of expression" refers to a natural or synthetic compound that has a biological effect to inhibit the expression of a gene. In a preferred embodiment of the invention, said inhibitor of gene expression is a siRNA, an antisense oligonucleotide or a ribozyme. For example, antisense oligonucleotides, including anti-sense RNA molecules and anti-sense DNA molecules, would act to directly block the translation of mineralocorticoid receptor mRNA by binding thereto and thus preventing protein translation or increasing mRNA degradation, thus decreasing the level of mineralocorticoid receptor, and thus activity, in a cell. For example, antisense oligonucleotides of at least about 15 bases and complementary to unique regions of the mRNA transcript sequence encoding mineralocorticoid receptor can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Small inhibitory RNAs (siRNAs) can also function as inhibitors of expression for use in the present invention. mineralocorticoid receptor gene expression can be reduced by contacting a subject or cell with a small double stranded RNA (dsRNA), or a vector or construct causing the production of a small double stranded RNA, such that mineralocorticoid receptor gene expression is specifically inhibited (i.e. RNA interference or RNAi). Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and preferably cells expressing mineralocorticoid receptor. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

According to the invention, the active ingredients of the invention (e.g. MR antagonist or inhibitor of expression) are administered to the subject in a therapeutically effective amount. By a "therapeutically effective amount" is meant a sufficient amount of the active ingredient for preventing or reducing glucocorticoid-induced corneal or skin thinning at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination with the active ingredients; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

In some embodiment, the glucocorticoid and the MR antagonist are to be used simultaneous or sequentially within a given time. The MR antagonist can be applied in either order, e.g. the MR antagonist can be applied first and then the glucocorticoid can be applied or vice versa. It is obvious that when a composition comprising both the MR antagonist and glucocortocoid is used both components will be applied at the same time.

Accordingly, a further aspect of the invention relates to a pharmaceutical composition comprising an active ingredient of the invention (i.e. a MR antagonist or inhibitor of gene expression) for use in a method for preventing or reducing glucocorticoid-induced conical or skin thinning in a subject in need thereof.

According to the invention, it may be desirable to administer the active ingredient of the invention in admixture with a topical pharmaceutically or cosmetically acceptable carrier. The topical pharmaceutically acceptable carrier is any substantially nontoxic carrier conventionally usable for topical administration of pharmaceuticals in which the active ingredient of the invention will remain stable and bioavailable when applied directly to skin. For example, carriers such as those known in the art effective for penetrating the keratin layer of the skin into the stratum corneum may be useful in delivering the active ingredient of the invention to the area of interest. Such carriers include liposomes. Active ingredient of the invention can be dispersed or emulsified in a medium in a conventional manner to form a liquid preparation or mixed with a semi-solid (gel) or solid carrier to form a paste, powder, eyedrop, ointment, cream, lotion or the like.

Suitable topical pharmaceutically acceptable carriers include water, buffered saline, petroleum jelly (vaseline), petrolatum, mineral oil, vegetable oil, animal oil, organic and inorganic waxes, such as microcrystalline, paraffin and ozocerite wax, natural polymers, such as xanthenes, gelatin, cellulose, collagen, starch, or gum arabic, synthetic polymers, alcohols, polyols, and the like. The carrier can be a water miscible carrier composition. Such water miscible, topical pharmaceutically acceptable carrier composition can include those made with one or more appropriate ingredients outset of therapy.

It may be desirable to have a delivery system that controls the release of active ingredient of the invention to the skin and adheres to or maintains itself on the skin for an extended period of time to increase the contact time of the active ingredient of the invention on the skin. Sustained or delayed release of active ingredient of the invention provides a more efficient administration resulting in less frequent and/or decreased dosage of active ingredient of the invention and better patient compliance. Examples of suitable carriers for sustained or delayed release in a moist environment include gelatin, gum arabic, xanthane polymers. Pharmaceutical carriers capable of releasing the active ingredient of the invention when exposed to any oily, fatty, waxy, or moist environment on the area being treated, include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like. Controlled delivery systems are described, for example, in U.S. Pat. No. 5,427,778 which provides gel formulations and viscous solutions for delivery of the active ingredient of the invention to a skin site. Gels have the advantages of having a high water content to keep the skin moist, the ability to absorb skin exudate, easy application and easy removal by washing. Preferably, the sustained or delayed release carrier is a gel, liposome, microsponge or microsphere.

Topical administration for cutaneous treatment is accomplished via a topically applied solution, cream, ointment, gel or other suitable formulation healing bandage which can then be applied to the skin such that the active ingredient of the invention composition contacts the skin. Examples of suitable transdermal devices are described, for instance, in U.S. Pat. No. 4,818,540. The active ingredient of the invention can be mixed with a pharmaceutically acceptable cream, applied to the skin, and covered with an occlusive dressing. Alternatively, the skin area can be irrigated or soaked with a solution of the active ingredient of the invention. The solution will be applied two to twelve times per day. For transdermal application, the active ingredient of the invention is formulated in a composition capable of allowing the active ingredient of the invention to penetrate the skin. Such compositions are applied directly to the skin or incorporated into a protective carrier such as a transdermal or "patch" device. The active ingredient of the invention formulations for transdermal administration can be used to coat the fibers of an absorbent gauze dressing.

In a particular embodiment, the pharmaceutical composition of the invention for treating cornea or anterior segment of the eye is an ophthalmic drop or an ophthalmic ointment. The eye drop is provided in any formulation generally used, for example, in the form of an aqueous eye drop such as aqueous eye drop solution, aqueous eye drop suspension, viscous eye drop solution, solubilized eye drop solution and the like, or in the form of a non-aqueous eye drop such as a non-aqueous eye drop solution, non-aqueous eye drop suspension and the like. When the composition is prepared as an aqueous eye drop, it preferably contains an additive which is usually used in an aqueous eye drop. The examples of such an additive include preservatives, isotonic agents, buffering agents, stabilizer, pH regulators or the like. When the composition is used in a form of an eye ointment, it includes any formulations usually used. For example, it can be easily produced by optionally heating an eye ointment base and mixing it with an active ingredient of the invention. The active ingredient of the invention may be optionally dissolved or suspended in a suitable solvent, for example, sterilized pure water, distilled water for injection, vegetable oil such as castor oil and the like, before mixing with the eye ointment base. The examples of the eye ointment base agent include purified lanolin, vaseline, plastibase, liquid paraffin and the like. The above-mentioned preservative, stabilizer and the like can be optionally blended provided the object of the present invention is not hurt.

A further aspect of the invention relates to a topical pharmaceutical composition (i.e. as above described) comprising an amount of at least one glucocorticoid and an amount of at least one MR antagonist (or inhibitor of MR expression) for use in a method for treating an inflammatory skin disease or an inflammatory disease of the cornea or of the anterior segment of the eye in a subject in need thereof.

The invention will be further illustrated by the following figures and examples. However, these examples and figures should not be interpreted in any way as limiting the scope of the present invention.

FIGURES

EXAMPLE

Figure 1:
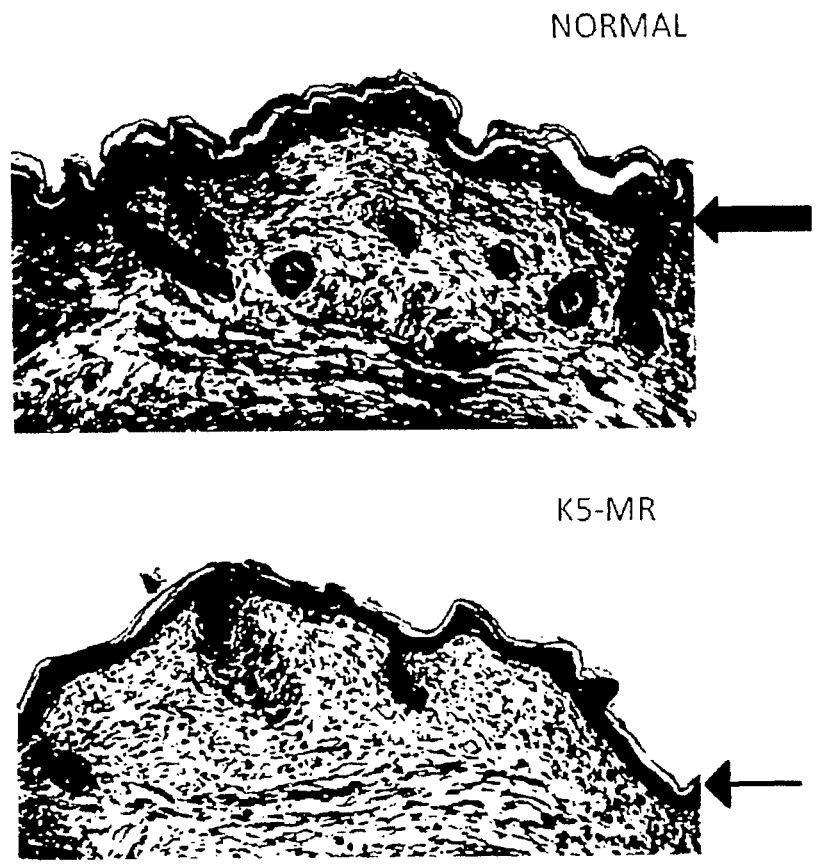
FIG. 1 shows that K5-MR newborn mice exhibit drastic reduction of the thickness of the epidermis (arrow).

Mice with MR overexpression in keratinocytes are not viable, and die shortly after birth (Sainte Marie Y, Toulon A, Pairs R, Maubec E, Cherfa A, Grossin M, et al. *Targeted skin overexpression of the mineralocorticoid receptor in mice causes epidermal atrophy, premature skin barrier formation, eye abnormalities, and alopecia. Am J Pathol.* 2007; 171(3): 846-60); the thickness of the epidermis was noticeably reduced (FIG. 1). To test whether the reduced epidermal thickness is related to excessive MR activation in this mouse model, we administered an antagonist of the mineralocorticoid receptor during pregnancy of the mice. In the two litters originating from pregnant mice that received Canrenoate (MR antagonist) all along pregnancy, the double-transgenic pups had normal skin appearance and histologically normal epidermal thickness. These results indicate that excess MR in keratinocytes leads to reduced epidermal thickness that is aggravated at birth. The question arises to know which MR ligand activates the MR in this condition. Because of the absence of HSD2 (the enzyme that inactivates glucocorticoids) in the epidermis (Kenouch S, Lombes M, Delahaye F, Eugene E, Bonvalet J P, Farman N. *Human skin as target for aldosterone: coexpression of mineralocorticoid receptors and 11 beta-hydroxysteroid dehydrogenase. J Clin Endocrinol Metab.* 1994: 79(5): 1334-41), it is likely that MR bound ligand is endogenous corticosterone, rather than aldosterone.

Figure 2:
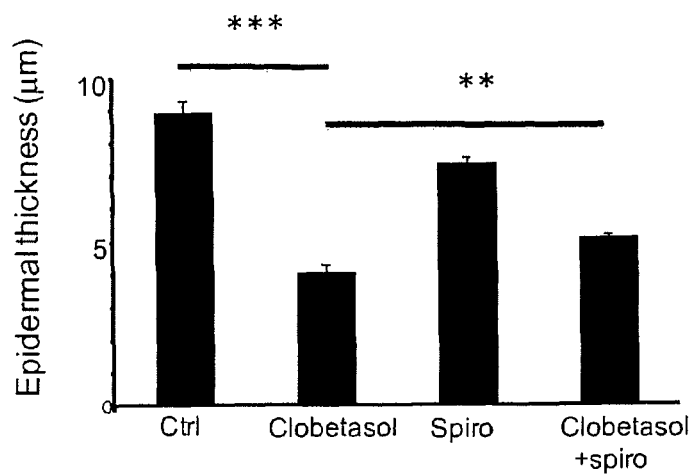
FIG. 2 shows that after 7 days of treatment, the reduction in epidermal thickness induced in mice by the glucocorticoid clobetasol was limited when spironolactone was administered topically.

In another set of experiments, we used normal adult mice that were treated by application of glucocorticoid (clobetasol, as 0.1 mM ethanol solution) alone or together with spironolactone (10 mM) over the back pelage, during 7 days. Clobetasol induced a drastic reduction of epidermal thickness, reproducing the well-known glucocorticoid-induced skin atrophy (Schoepe S, Schacke H, May E, Asacullah K. *Glucocorticoid therapy-induced skin atrophy. Exp Dermatol.* 2006; 15(6): 406-20). Spironolactone added to the clobetasol solution significantly increased epidermal thickness (FIG. 2), while spironolactone alone had no effect.

Figure 3:
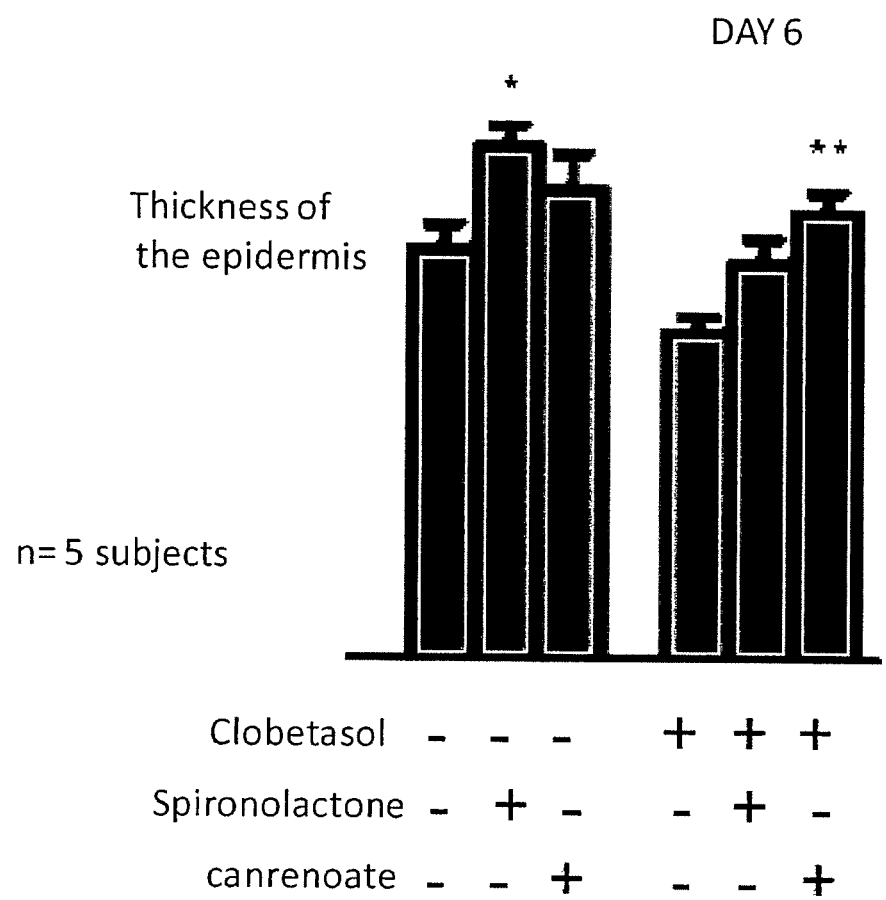
FIG. 3 shows that MR blockade improves the gluco-induced reduction in epidermal thickness in organotypic culture of human skin.

Human skin explants grown as organotypic culture represent a valuable model to study ex vivo epidermal homeostasis. Skin punches (3 mm) were made (accupunch) from human skin (discarded during mammary gland surgery) and placed in organotypic culture as explants (air/liquid interface) in 2 ml DMEM and 10% decomplemented charcoal-stripped foetal bovine scrum to remove steroids for 6 days, in the presence of clobetasol (100 nM) alone or together with spironolactone or canrenoate (potassium canrenoate) (10 micromolar) or solvent alone (0.1% ethanol). The results (FIG. 3) show that the two MR blockers increase the thickness of the epidermis.

REFERENCES

Throughout this application, various references describe the state of the art to which this invention pertains. The disclosures of these references are hereby incorporated by reference into the present disclosure.

The invention claimed is:

1. A method for preventing or reducing glucocorticoid-induced corneal thinning in a subject in need thereof comprising
administering to the subject a therapeutically effective amount of a mineralocorticoid receptor antagonist, wherein said therapeutically effective amount is sufficient to prevent or reduce the glucocorticoid-induced corneal thinning in the subject.

2. The method according to claim 1 wherein the subject suffers of an ocular disease selected from the group consisting of uveitis, blepharitis, conjunctivitis, scleritis, and post-operative inflammation.

3. The method of claim 1 wherein the subject was treated with a glucocorticoid selected from the group consisting of 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, anecortave acetate or a derivative of any of these glucocorticoids.

4. The method of claim 1 wherein the mineralocorticoid receptor antagonist is a steroidal mineralocorticoid receptor antagonist or a non-steroidal mineralocorticoid receptor antagonist.

5. The method of claim 4 wherein the mineralocorticoid receptor antagonist is spironolactone or eplerenone.

6. A method for preventing or reducing glucocorticoid-induced corneal thinning in a subject in need thereof, comprising
administering to the subject a therapeutically effective amount of a mineralocorticoid receptor antagonist, wherein said therapeutically effective amount is sufficient to prevent or reduce the glucocorticoid-induced corneal thinning in the subject,
wherein the mineralocorticoid receptor antagonist is topically administered to the subject.

* * * * *